(12) United States Patent
Thelen et al.

(10) Patent No.: US 12,605,148 B2
(45) Date of Patent: Apr. 21, 2026

(54) CALIBRATION TOOL FOR TISSUE TENSION SENSOR

(71) Applicant: Wisconsin Alumni Research Foundation, Madison, WI (US)

(72) Inventors: Darryl Thelen, Madison, WI (US); Alex Reiter, Madison, WI (US); Peter Adamczyk, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 574 days.

(21) Appl. No.: 18/061,141

(22) Filed: Dec. 2, 2022

(65) Prior Publication Data

US 2024/0180530 A1      Jun. 6, 2024

(51) Int. Cl.
*A61B 5/103* (2006.01)
*A61B 8/00* (2006.01)

(52) U.S. Cl.
CPC .............. *A61B 8/58* (2013.01); *A61B 5/1036* (2013.01); *A61B 8/485* (2013.01); *A61B 2560/0238* (2013.01)

(58) Field of Classification Search
None
See application file for complete search history.

(56) References Cited

U.S. PATENT DOCUMENTS

| | | | |
|---|---|---|---|
| 5,415,176 A * | 5/1995 | Sato ...................... | G01G 19/50 600/587 |
| 10,555,690 B1 * | 2/2020 | Al-Askar ............. | A61B 5/1072 |
| 2002/0148654 A1 * | 10/2002 | Montagnino .......... | G01G 19/44 177/245 |
| 2013/0032413 A1 * | 2/2013 | Smith .................... | G01G 19/50 177/1 |
| 2017/0055836 A1 * | 3/2017 | Thelen ................. | A61B 5/4533 |
| 2017/0188856 A1 * | 7/2017 | Banet .................... | A61B 5/349 |

* cited by examiner

*Primary Examiner* — Etsub D Berhanu
(74) *Attorney, Agent, or Firm* — Boyle Fredrickson S.C.

(57) ABSTRACT

A calibration system for a tensiometer provides a platform having a footplate with a fulcrum bar for providing a located force on an individual's leg to be used in conjunction with a tissue stress sensor attached near a tendon or ligament of the leg to establish a relationship between force on the tendon or ligament and the tissue stress sensor output for simplified calibration.

13 Claims, 3 Drawing Sheets

CALIBRATION TOOL FOR TISSUE TENSION SENSOR

STATEMENT REGARDING FEDERALLY SPONSORED RESEARCH OR DEVELOPMENT

This invention was made with government support under W81XWH-21-2-0006 awarded by the ARMY/MRMC and under AR074897 awarded by the National Institutes of Health. The government has certain rights in the invention.

CROSS REFERENCE TO RELATED APPLICATION

Background of the Invention

The present invention relates to sensors for measuring tissue loads (e.g., stress, tension, or the like) using shear waves passing through the tissue and, in particular, an apparatus for calibrating the tissue load sensor to a particular individual.

The ability to measure the absolute stress that ligaments, tendons, or muscle experience in vivo has considerable value in medical research and rehabilitative medicine. Prior techniques used in research settings are highly invasive and include insertion of a "buckle transducer" around the tissue or the threading of a fiber optic sensor through the tissue and detecting changes in light transmission associated with tension.

As an alternative, tissue stress can often be inferred from measurements of force (e.g., torque) applied to a limb and using inverse dynamics to assess results of that applied force on the tissue. Tissue cross-sections can then be measured to convert the force to a stress value. This approach is cumbersome, however, and requires many assumptions and greatly restricts the availability of these measurements outside of laboratory environments.

U.S. Pat. No. 10,631,775, entitled "Apparatus for Dynamic Stress Measurement," assigned to the present assignee, and hereby incorporated by reference, describes a method for characterizing relative stress in ligaments, tendons, and muscles using the propagation of a shear wave. An apparatus for implementing this technique can be attached to an individual for dynamic stress measurements in real time.

Such shear wave speed measurements can provide a measure of absolute stress by calibrating the measurements to a particular individual. In this calibration process, shear wave speeds are associated with particular quasi-static loadings of the tissue to determine a calibration factor relating the two. For example, measurements of absolute stress of the Achilles tendon can be determined from a known torque applied to the individual's ankle, measurement of the individual's ankle moment arm (between the tendon and the ankle pivot point), and tendon cross-section (for example, by ultrasonic measurement). Calibration factors can then be determined from the relationship between Achilles tendon stress and simultaneously measured shear wave speeds. These calibration factors are then used to convert shear wave speed to absolute load values such as absolute tendon force or absolute stress values during other movements independent of the calibration process.

SUMMARY OF THE INVENTION

The present invention provides a calibration tool that simplifies calibration of shear wave speed sensors. The tool provides a platform with one or more force plates and upwardly extending handles that may be used to balance the individual on the force plates. Each force plate includes a fulcrum bar that simply and quickly defines the location of a force vector needed for the calibration process. The individual, by shifting weight between feet or pushing down or pulling up on the handles, promotes a range of forces on tendons of the lower limbs instrumented with a shear wave sensor. An attached controller then establishes a functional relationship between shear wave speed and force which can be variously converted to tendon tension, stress, or the like.

More specifically, in one embodiment, the invention provides a tissue tensiometer calibration system having a base supportable against a horizontal surface and a footplate positioned above and connected to the base by one or more force sensors providing an electrical force output signal indicating a force on the footplate. The footplate includes a fulcrum bar attached to the upper surface of the footplate to provide an upwardly and laterally extending ridge to isolate the weight of an individual standing on the footplate to a force at a single line on the ridge. The calibration system also includes a support bar attached to the base to provide a handle positionable above the base at a height to be held by an individual standing on the footplate.

It is thus a feature of at least one embodiment of the invention to provide a tool for simplified calibration of tension sensors amenable to the need to define a set of force vectors on a limb at a specific location enforced by the fulcrum bar.

The handle may include a horizontal grip for receiving the fingers of a hand of the individual standing on the footplate to pull upward on the handle.

It is thus a feature of at least one embodiment of the invention to provide not only for balancing by the individual but to allow the individual to pull up or push downward on the handles to create a larger range of forces.

The support bar may be adjustable in length at multiple stops.

It is thus a feature of at least one embodiment of the invention to allow a convenient location of the handles for improved support for individuals of different heights while still offering a particular point for force application.

The support bar may be releasably attached to the base.

It is thus a feature of at least one embodiment of the invention to allow convenient storage of the calibration tool when not used by removing the handles reducing the height of the tool for easy storage.

The calibration system may include a left and right support bar positioned on opposed lateral sides of the footplate each providing a handle positionable above the base at heights to be held by an individual standing on the footplate.

It is thus a feature of at least one embodiment of the invention to provide improved balance to the individual when rocking from side to side during a calibration measurement.

Similarly, the calibration system may include left and right footplates each with fulcrum bars.

It is thus a feature of at least one embodiment of the invention to allow rapid calibration of two sensors when bilateral measurements are to be made The tensiometer calibration may further include a positioner for guiding a positioning of the individual's limbs with respect to the base plate.

It is thus a feature of at least one embodiment of the invention to provide a calibration tool that permits accurate location of the individual's leg joints necessary for the precise calibration.

These particular objects and advantages may apply to only some embodiments falling within the claims and thus do not define the scope of the invention.

DETAILED DESCRIPTION OF THE PREFERRED EMBODIMENT

Figure 1:
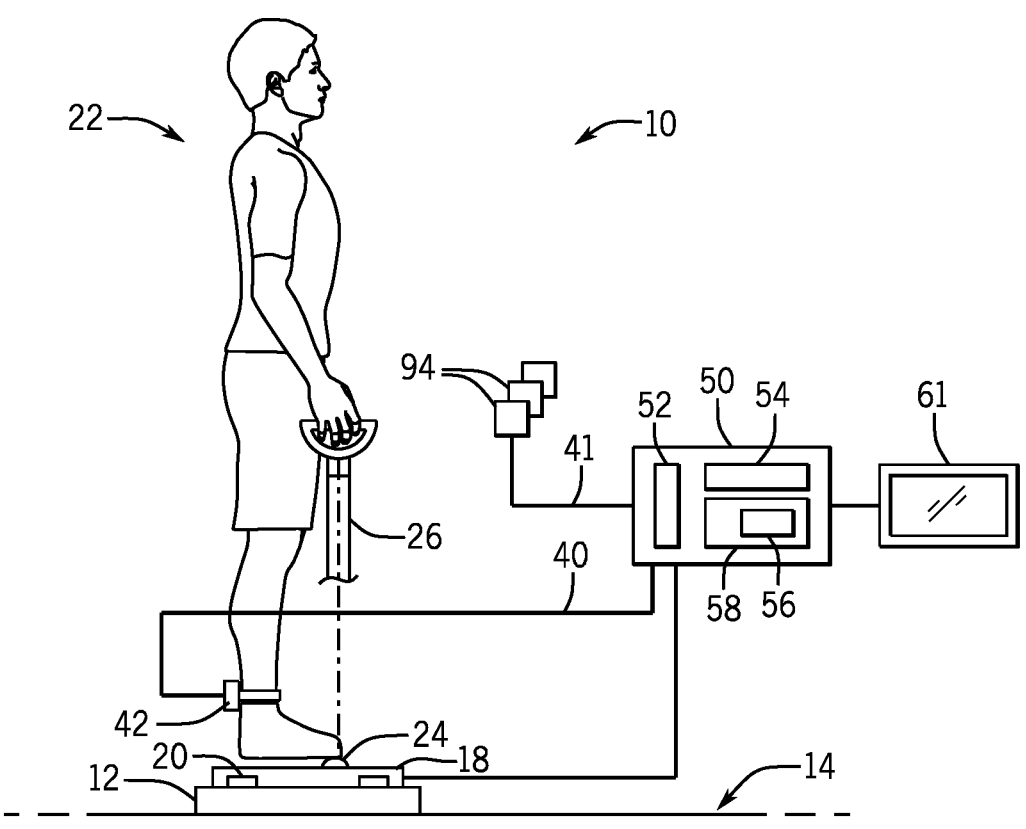
FIG. 1 side elevational view of an individual using the platform of the present invention while gripping side handles (shown in fragment) to provide shear wave speed and limb forces to an associated controller.
Figure 3:
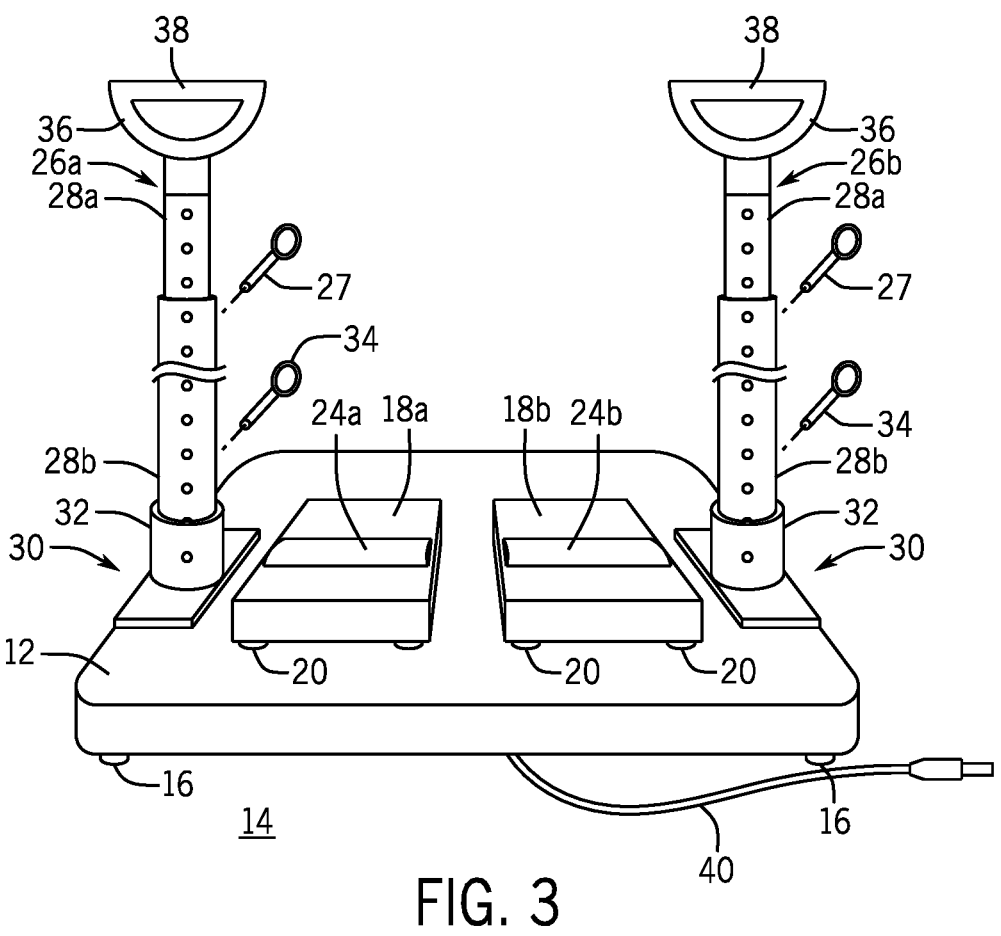
FIG. 3 is a front perspective view of the platform showing left and right force plates, fulcrum bars, and extendable handles.

Referring now to FIGS. 1 and 3, a tensiometer calibration system 10 of the present invention may provide a base 12 for resting on a horizontal surface such as the floor 14 and providing a generally rigid plate presenting an upper horizontal surface and having, for example, elastomeric feet 16 on its lower surface for engaging the floor 14.

Positioned above the base 12 are laterally separated left and right footplates 18a and 18b spaced from the base 12 by load cells 20, for example, positioned at each of four corners of a rectangular footplate 18. The footplates 18 are sized in area generally so that they could receive at least a portion of a user's feet and support a weight of a user 22 when the user stands on the upper surfaces of the footplates 18. The centers of the footplates 18 may be laterally separated to accommodate the separation of the feet of the user 22 with a normal standing posture.

Each of the footplates 18 provides a transversely aligned and laterally extending fulcrum bar 24a or 24b, each fulcrum bar 24 presenting an upwardly facing ridge rising from the upper surface of the footplates 18 and roughly centered along the transverse extent of the footplates 18. The height of the fulcrum bars 24 is such as to allow the weight of the user 22 to be fully supported on the fulcrum bar 24 without the user's feet contacting the exposed surface of the footplates 18, for example, providing a height of at least ½ inch or at least 1 inch or more.

In one embodiment, the fulcrum bars 24 will have an upwardly convex cross-section (taken along a lateral axis), for example, being a hemi circle with a radius of ½ inch, so as to concentrate a downward force by the user's foot to within a limited transverse zone along the user's foot, for example, a zone having a transverse distance of 1½ inch or less or desirably 1 inch or less. The fulcrum bars 24 may be a rigid material relying on the cushioning of the user's shoes for comfort or may provide a cushion or elastomeric inset in their upper surfaces.

Flanking the footplates 18 on either lateral side, and preferably positioned in transverse alignment with the fulcrum bars 24 or slightly forward from the fulcrum bars 24, are a set of upwardly extending handles 26a and 26b. The handles 26 may each be comprised of a pair of telescoping tubes 28a and 28b with the outer diameter of tube 28a being sized to slide smoothly along the inner diameter of tube 28b between a total length of approximately 20 inches and 40 inches. A particular extension between the tubes 28a and 28b may be locked by means of locking pins 27 which provide positive stops by being inserted through diametrically extending and aligned holes in each of the tubes 28a and 28b. The holes may be generally spaced at increments of 1 inch along their lengths to provide a corresponding degree of adjustment.

A lower end of each tube 28b may be attached to the upper surface of the base 12 by a rigid socket 30 including an upwardly open cylindrical collar 32 receiving the outer diameter of each tube 28 and retaining the tube 28 therein by means of a locking pin 34 passing through diametrically extending and aligned holes in the bottom of the tube 28b and corresponding portions of the socket 30. Removal of the locking pin 34 allows ready disassembly of the handles 26 from the base 12 for storage.

At an upper end of each handle 26, as attached to the upper end of tubes 28, are grips 36 (shown rotated 90° with respect to actual orientation in FIG. 3 for clarity). The grips 36 provide a horizontal gripping bar 38 that may be grasped by the user 22 when the user is standing on the footplates 18 and which allow the user to readily pull upward on the grips 36 to increase the force on the footplates 18 under certain calibration protocols. As such, the horizontal gripping bar 38 may receive all of the fingers of the user's hand with the thumb wrapped in the opposite direction and the palm resting on top of the horizontal gripping bar 38, allowing upward or downward pressure.

Referring to FIG. 1, signals from each of the load cells 20 for each of the footplates 18a and 18b may be combined according to the techniques understood in the art to yield a total downward force, independently, on each of the footplates 18a and 18b. This force may be expressed by an electrical signal that may be communicated via cable 40 (or by wireless connection) to an electronic computer 50.

As will be discussed in greater detail below, the force communicated by the electrical signal and having a specific angle and location on limb of the user 22 can be used to deduce a corresponding force on tissue of interest. For example, the force on the user's foot at the fulcrum bar 24 affects the tension of the user's Achilles tendon as shown in FIG. 1. This deduced force on the tissue of interest may be used to calibrate a tissue stress sensor 42 placed on that same tissue, for example, on the Achilles tendon to relate (calibrate) the value output by the tissue stress sensor 42.

A tissue stress sensor 42 suitable for use with the present invention is described in US patent applications 2019/0200900 and 2017/0055836 assigned to the assignee of the present application and hereby incorporated by reference. Such sensors can measure axial stress or similar properties in a stressed tendon or ligament by mechanical excitation of a shear wave in the tendon or ligament measured at two or more different lateral positions to derive a shear wave propagation speed. As shown in FIG. 1, the tissue stress sensor 42 may communicate its uncalibrated values (shear wave speed) to the computer 50 via cable 41 or by wireless connection.

The computer 50 may include an interface 52 for communicating with the cables 40 and 41 and one or more electronic processors 54 executing a program 56 contained in computer memory 58 output from the computer 50, and inputs for the program 56 may be provided by a user terminal 61 of the type generally understood in the art.

The program 56 receiving output from the tissue stress sensor 42 and simultaneously from the load cells 20 deduces a function relating these values to provide a calibration of the tissue stress sensor 42. For example, the shear wave propagation speed of the tissue stress sensor 42 placed on the Achilles tendon may be calibrated to axial stress by having the user 22 stand on the footplates 18, for example, as shown in FIG. 1 with the ball of the user's feet on the fulcrum bars 24. The user is then instructed to vary the weight on each footplate, for example, by rocking from side to side or pulling down or up on the handles 26.

Figure 2:
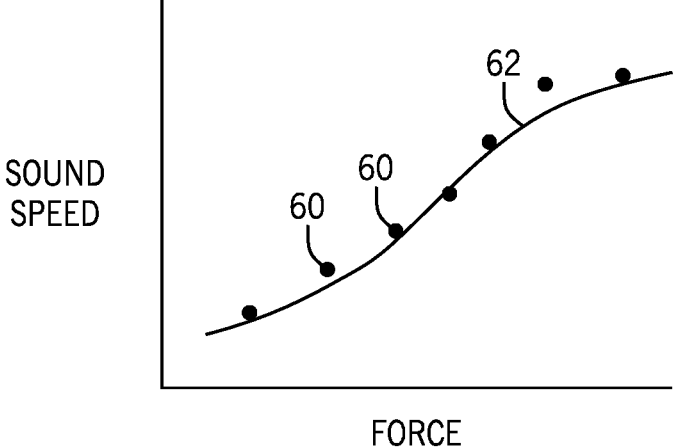
FIG. 2 is plot of limb force versus shear wave speed that may be produced by the controller FIG. 1.

Referring now also to FIG. 2, during that time, multiple samples 60 are acquired by the computer each one having a dimension of wave speed measured by the tissue stress sensor 42, one dimension of force measured by the footplate 18 of the corresponding ankle having the tissue stress sensor 42. It will be understood that this process can also be accomplished simultaneously for two different tissue stress sensors 42 on different angles associated with different footplates 18*a* and 18*b*.

The samples 60 may be fit to a curve 62 that provides a function relating wave speed to force on the footplate 18, and thus the first level of calibration.

Figure 5:
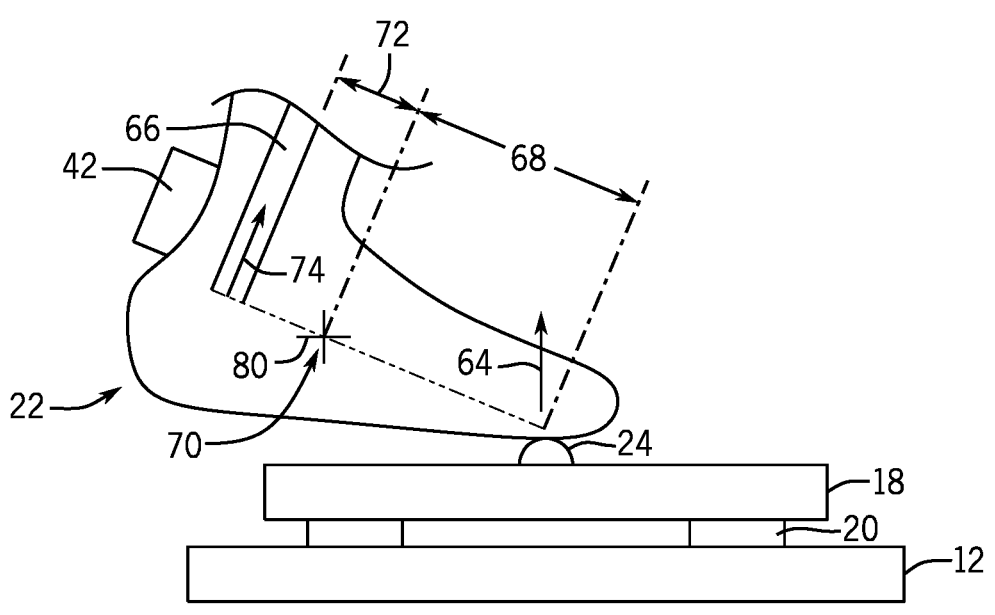
FIG. 5 is a fragmentary diagrammatic representation of a user's foot showing various dimensions used for calibration and the alignment of the ankle joint using the positioning laser of FIG. 4 in one application.

Referring now to FIG. 5, it will be understood that this force 64 can be converted to a stress on the tissue being measured 66 by the tissue stress sensor 42 (to provide a direct calibration between wave speed and tissue stress) by a measurement of the length of a first lever arm 68 between the upward force on the foot generated by the fulcrum bar 24 and the ankle joint 70 and the length of a second lever arm 72 between the ankle joint and the attachment of the tissue being measured 66. These measures plus the angle of the force 64 and 74 to the respective lever arms yields actual force 74 on the tissue being measured 66. The cross-section of the tissue being measured 66 can then be estimated or measured to provide a stress conversion. More generally, the calibration may be to any standard force-related dimension including force, stress, tension, and the like.

Figure 4:
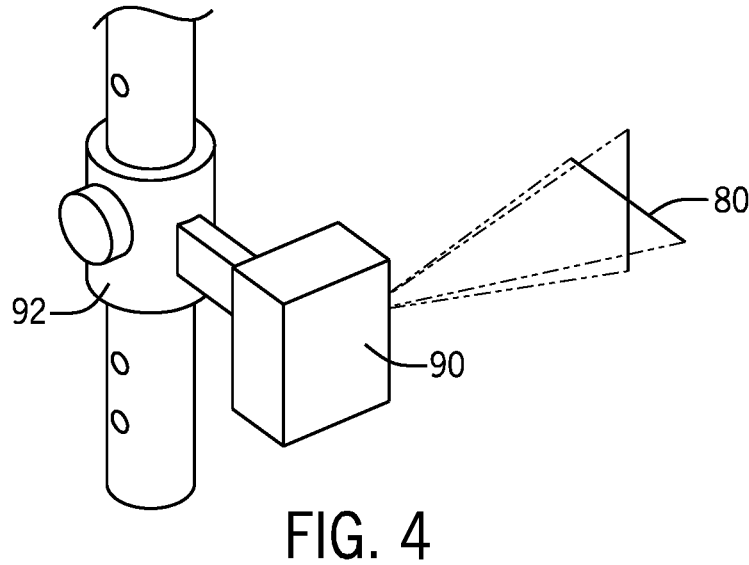
FIG. 4 is a fragmentary perspective view of one handle of FIG. 1 showing a positioning laser attached thereto.

Referring now to FIG. 4, this latter calibration can be simplified by providing a fiducial guide in the form of a laser crosshair 80 that may be projected laterally, for example, to a desired location joint centers of the ankle joint 70 (shown in FIG. 5) and knee joint 82 (shown in FIG. 6) to ensure that the assumptions of these geometric calculations are preserved during the calibration process, for example, instructing the user 22 to keep the alignment of these crosshairs on the appropriate locations. The laser crosshairs 80 may be produced by a laser projector 90 providing an adjustable height and rotational clamp 92 that can attach to appropriate locations on the handles 26.

Figures 6, 7:
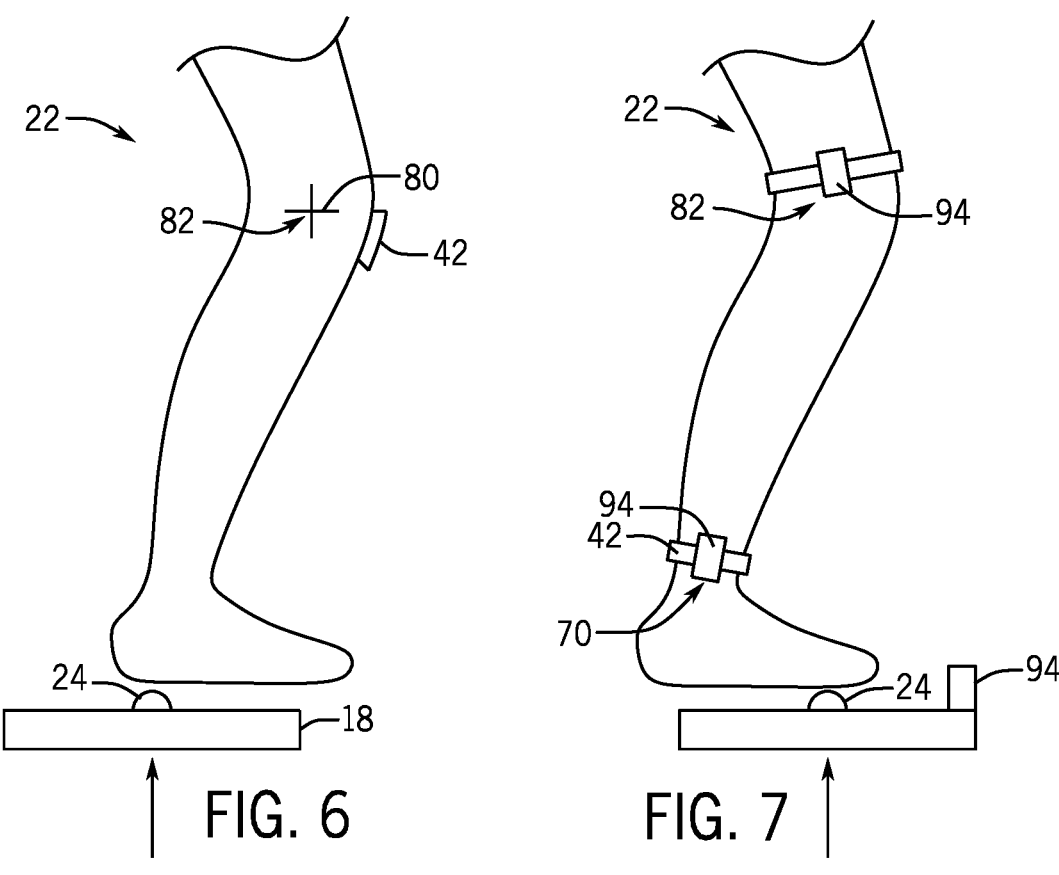
FIG. 6 is a fragmentary view of a user's leg for a measure of the patellar ligament.
FIG. 7 is a figure similar to FIG. 6 showing measurement of the Achilles tendon using electronic position sensors.

Referring now to FIG. 6, it will be appreciated that the present calibration system is not limited to measurements of the Achilles tendon, for example, in the foregoing discussion but can be used for other measurements, for example, of the patellar tendon. Here the user is instructed to place his or her heel on the fulcrum bar 24, to align his or her knee joint 82 with a desired location of a laser crosshair 80 and the tissue stress sensor 42 is placed over the patella tendon to establish wave speed/force calibration as discussed above.

Referring now to FIG. 7, it will be appreciated that the function of the laser crosshairs 80 may be augmented or replaced by absolute position sensors 94, for example, placed on the ankle joint 70 and knee joint 82 and footplate 18, or these position sensors 94 may be used selectively to replace particular manual measurements. In one embodiment the position sensors 94 are inertial measurement units (IMU's) commercially available under the trade name MVN Awinda from XSens B.V. of the Netherlands and provide for three-axis absolute angular orientation measurements using a 3-D rate gyroscope, a 3-D accelerometer, a 3-D magnetometer, and software to allow extraction of the relative angular measurements. Each of the position sensors 94 may also provide position signals directly to the computer 50 for the purpose of these calculations.

While a specific example of the invention has been provided, the invention contemplates use with a variety of different muscles/tendons (alone or in combination) including but not limited to biceps femoris (hamstrings); medial and/or lateral hamstring tendons (behind the knee, inside and outside); tibialis anterior-patellar tendon; and both medial and lateral hamstrings.

The above embodiment describes the use of two footplates 18 and two handles 26; however, it will be understood that a simplified version of the invention may provide for only one footplate 18 and/or only one handle 26. It will be further understood that the laser and the other positioner sensors all operate as positioners for limb positioning which may be alternatively a non-laser projector, a mechanical pointer, or a brace having one end fixed with respect to the base and the other end locatable at the desired position of the limb.

Certain terminology is used herein for purposes of reference only, and thus is not intended to be limiting. As noted, "muscle tissue" refers collectively to any of muscles, tendons or ligaments associated with work measurements. The terms such as "upper", "lower", "above", and "below" refer to directions in the drawings to which reference is made. Terms such as "front", "back", "rear", "bottom", and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order or quantity unless clearly indicated by the context.

When introducing elements or features of the present disclosure and the exemplary embodiments, the articles "a", "an", "the" and "said" are intended to mean that there are one or more of such elements or features. The terms "comprising", "including", and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a computer" or the like can be understood to include one or more microprocessors that can communicate in a stand-alone and/or a distributed environment(s), and can thus be configured to communicate via wired or wireless communications with other processors, where such one or more processors can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A tissue tensiometer calibration system comprising:
a base supportable against a horizontal surface;
a footplate positioned above and connected to the base by one or more force sensors sensing a downward force on the footplate with respect to the base, the one or more force sensors providing an electrical force output signal indicating a force on the footplate;
a fulcrum bar attached to an upper surface of the footplate to provide an upwardly and laterally extending ridge to isolate a downward force of a weight of an individual standing on the footplate to a downward force on the ridge; and
a support bar attached to the base to provide a handle positionable above the base at a height to be held by the individual standing on the footplate; and
further including a tissue stress sensor positionable on tissue of the individual to sense the effects of stress in the tissue on wave speed through the tissue to provide an output signal based on wave speed; and
further including an electronic computer executing a stored program to match the output signal based on wave speed to the output signal indicating a force on the footplate to determine a calibration function for calibrating the tissue stress sensor.

2. The tissue tensiometer calibration system of claim 1 wherein the handle includes a horizontal grip for receiving fingers of a hand of the individual standing on the footplate to pull upward on the handle.

3. The tissue tensiometer calibration system of claim 1 wherein the support bar is adjustable in length at multiple stops.

4. The tissue tensiometer calibration system of claim 1 wherein the support bar is releasably attached to the base.

5. The tissue tensiometer calibration system of claim 1 including a second support bar, the support bar and the second support bar together providing a left and right support bar positioned on opposed lateral sides of the footplate each providing a handle positionable above the base at heights to be held by the individual standing on the footplate.

6. The tissue tensiometer calibration system of claim 1 including a second footplate positioned above and connected to the base by a second one or more force sensors sensing a downward force on the second footplate with respect to the base, the second one or more force sensors providing a second electrical force output signal indicating a force on the second footplate; and
further including a second fulcrum bar, the fulcrum bar and the second fulcrum bar together providing left and right fulcrum bars attached respectively to the upper surfaces of the footplate and second footplate to provide respective upwardly and laterally extending ridges to isolate the downward force of the weight of the individual standing on the footplate and second footplate to downward forces on the respective ridges.

7. The tissue tensiometer calibration system of claim 1 wherein the fulcrum bar is configured to contact a foot of a human over a transverse width of less than 2 inches.

8. The tissue tensiometer calibration system of claim 1 wherein the fulcrum bar provides an upwardly extending convex cross-section across a lateral axis.

9. The tissue tensiometer calibration system of claim 1 further including a positioner for guiding a positioning of the individual's joint centers with respect to the base plate.

10. A method of calibrating a tissue tensiometer having:
a base supportable against a horizontal surface;
a footplate positioned above and connected to the base by one or more force sensors sensing a downward force on the footplate with respect to the base, the one or more force sensors providing an electrical force output signal indicating a force on the footplate;
a tissue stress sensor positionable on tissue of an individual to sense the effects of stress in the tissue on wave speed through the tissue to provide an output signal based on wave speed;
a fulcrum bar attached to an upper surface of the footplate to provide an upwardly and laterally extending ridge to isolate a downward force of a weight of the individual standing on the footplate to a downward force on the ridge; and
a support bar attached to the base to provide a handle positionable above the base at a height to be held by the individual standing on the footplate;
the method comprising:
(a) positioning the individual to stand on the footplate with varying downward force to provide an output force signal from the one or more force sensors;
(b) receiving at an electronic computer a corresponding set of the output force signal and an output signal based on wave speed from the tissue stress sensor attached to the individual; and
(c) matching the output signal based on wave speed to the output force signal to determine a calibration function for calibrating the tissue stress sensor.

11. The method of claim 10 wherein step (a) varies the downward force on the footplate by at least one of: having the individual apply force to the handle; and having the individual rock back and forth between his or her left and right feet.

12. The method of claim 10 further including adjusting a height of the support bar to position the handle to be gripped by the individual in a standing position on the footplate with a gripping arm flexed.

13. The method of claim 10 further including the step of adjusting a positioner to guide the individual in positioning at least one joint of a leg of the individual during step (a) with respect to the base plate.

* * * * *